United States Patent
Mannheimer et al.

(10) Patent No.: US 7,848,891 B2
(45) Date of Patent: Dec. 7, 2010

(54) MODULATION RATIO DETERMINATION WITH ACCOMMODATION OF UNCERTAINTY

(75) Inventors: Paul D. Mannheimer, Danville, CA (US); Steven E. Pav, San Francisco, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 688 days.

(21) Appl. No.: 11/540,170

(22) Filed: Sep. 29, 2006

(65) Prior Publication Data

US 2008/0081325 A1    Apr. 3, 2008

(51) Int. Cl.
*G06F 19/00* (2006.01)
*G01N 33/50* (2006.01)
*A61B 5/0295* (2006.01)

(52) U.S. Cl. ............................. 702/19; 436/68; 600/322; 600/323

(58) Field of Classification Search .................. None
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,805,623 A | 2/1989 | Jöbsis |
| 4,911,167 A | 3/1990 | Corenman et al. |
| 4,936,679 A | 6/1990 | Mersch |
| 4,972,331 A | 11/1990 | Chance |
| 5,119,815 A | 6/1992 | Chance |
| 5,122,974 A | 6/1992 | Chance |
| 5,167,230 A | 12/1992 | Chance |
| 5,297,548 A | 3/1994 | Pologe |
| 5,351,685 A | 10/1994 | Potratz |
| 5,355,880 A | 10/1994 | Thomas et al. |
| 5,372,136 A | 12/1994 | Steuer et al. |
| 5,385,143 A | 1/1995 | Aoyagi |
| 5,482,036 A | 1/1996 | Diab et al. |
| 5,490,505 A | 2/1996 | Diab et al. |
| 5,503,148 A * | 4/1996 | Pologe et al. ............... 600/323 |
| 5,553,614 A | 9/1996 | Chance |
| 5,564,417 A | 10/1996 | Chance |
| 5,575,285 A | 11/1996 | Takanashi et al. |
| 5,630,413 A | 5/1997 | Thomas et al. |
| 5,632,272 A | 5/1997 | Diab et al. |
| 5,645,059 A | 7/1997 | Fein et al. |
| 5,645,060 A | 7/1997 | Yorkey |
| 5,685,299 A | 11/1997 | Diab et al. |
| 5,692,503 A | 12/1997 | Keunstner |
| 5,727,547 A | 3/1998 | Levinson et al. |
| 5,758,644 A | 6/1998 | Diab et al. |
| 5,769,785 A | 6/1998 | Diab et al. |
| 5,779,631 A | 7/1998 | Chance |
| 5,813,980 A | 9/1998 | Levinson et al. |
| 5,823,952 A | 10/1998 | Levinson et al. |
| 5,830,139 A | 11/1998 | Abreu |
| 5,842,981 A | 12/1998 | Larsen et al. |
| 5,851,179 A | 12/1998 | Rison et al. |
| 5,873,821 A | 2/1999 | Chance et al. |
| 5,934,277 A | 8/1999 | Mortz |
| 5,954,277 A | 9/1999 | Maciejewski et al. |
| 5,995,856 A | 11/1999 | Mannheimer et al. |
| 6,011,986 A | 1/2000 | Diab et al. |
| 6,018,673 A | 1/2000 | Chin et al. |
| 6,036,642 A | 3/2000 | Diab et al. |
| 6,064,898 A | 5/2000 | Aldrich |
| 6,081,735 A | 6/2000 | Diab et al. |
| 6,120,460 A | 9/2000 | Abreu |
| 6,134,460 A | 10/2000 | Chance |
| 6,157,850 A | 12/2000 | Diab et al. |
| 6,163,715 A | 12/2000 | Larsen et al. |
| 6,181,958 B1 | 1/2001 | Steuer et al. |
| 6,186,142 B1 * | 2/2001 | Schmidt et al. ......... 128/204.23 |
| 6,206,830 B1 | 3/2001 | Diab et al. |
| 6,222,189 B1 | 4/2001 | Misner et al. |
| 6,230,035 B1 | 5/2001 | Aoyagi et al. |
| 6,236,872 B1 | 5/2001 | Diab et al. |
| 6,263,222 B1 | 7/2001 | Diab et al. |
| 6,266,546 B1 | 7/2001 | Steuer et al. |
| 6,280,381 B1 * | 8/2001 | Malin et al. ................. 600/322 |
| 6,312,393 B1 | 11/2001 | Abreu |

(Continued)

FOREIGN PATENT DOCUMENTS

DE    102 13 692 A1    10/2003

(Continued)

OTHER PUBLICATIONS

Wukitsch et al. Pulse Oximetry: Analysis of Theory, Technology, and Practice Journal of Clinical Monitoring and Computing vol. 4, pp. 290-301 (1988).*

(Continued)

*Primary Examiner*—John S Brusca

(57) ABSTRACT

Embodiments of the present invention relate to a system and method for detecting a blood characteristic in a patient. Embodiments of the present invention may comprise detecting a first modulating signal at a first wavelength, detecting a second modulating signal at a second wavelength, and determining a relative amplitude of the first and second modulating signals. Further, embodiments of the present invention may comprise regressing the first and second modulating signals relative to one another, wherein a first uncertainty value in the first modulating signal and a second uncertainty value in the second modulating signal are accommodated.

32 Claims, 6 Drawing Sheets

U.S. PATENT DOCUMENTS

| | | |
|---|---|---|
| 6,339,715 B1 | 1/2002 | Bahr et al. |
| 6,374,129 B1 | 4/2002 | Chin et al. |
| 6,385,471 B1 | 5/2002 | Mortz |
| 6,397,091 B2 | 5/2002 | Diab et al. |
| 6,400,972 B1 | 6/2002 | Fine |
| 6,415,236 B2 | 7/2002 | Kobayashi et al. |
| 6,434,408 B1 | 8/2002 | Heckel |
| 6,438,399 B1 | 8/2002 | Kurth |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,591,122 B2 | 7/2003 | Schmitt |
| 6,594,513 B1 | 7/2003 | Jobsis et al. |
| 6,615,064 B1 | 9/2003 | Aldrich |
| 6,622,095 B2 | 9/2003 | Kobayashi et al. |
| 6,647,280 B2 | 11/2003 | Bahr et al. |
| 6,650,917 B2 | 11/2003 | Diab et al. |
| 6,658,277 B2 | 12/2003 | Wasserman |
| 6,662,030 B2 | 12/2003 | Khalil et al. |
| 6,671,526 B1 | 12/2003 | Aoyagi et al. |
| 6,671,528 B2 | 12/2003 | Steuer et al. |
| 6,675,031 B1 | 1/2004 | Porges et al. |
| 6,678,543 B2 | 1/2004 | Diab et al. |
| 6,690,958 B1 | 2/2004 | Walker et al. |
| RE38,476 E | 3/2004 | Diab et al. |
| 6,708,048 B1 | 3/2004 | Chance |
| 6,711,424 B1 | 3/2004 | Fine et al. |
| 6,711,425 B1 | 3/2004 | Reuss |
| RE38,492 E | 4/2004 | Diab et al. |
| 6,745,060 B2 | 6/2004 | Diab et al. |
| 6,748,254 B2 | 6/2004 | O'Neil et al. |
| 6,785,568 B2 | 8/2004 | Chance |
| 6,801,797 B2 | 10/2004 | Mannheimer et al. |
| 6,801,799 B2 | 10/2004 | Mendelson |
| 6,826,419 B2 | 11/2004 | Diab et al. |
| 6,845,256 B2 | 1/2005 | Chin et al. |
| 6,873,865 B2 | 3/2005 | Steuer et al. |
| 6,898,451 B2 | 5/2005 | Wouri |
| 6,898,452 B2 | 5/2005 | Al-Ali et al. |
| 6,949,081 B1 | 9/2005 | Chance |
| 6,961,598 B2 | 11/2005 | Diab |
| 6,983,178 B2 | 1/2006 | Fine et al. |
| 6,987,994 B1 | 1/2006 | Mortz |
| 6,993,372 B2 | 1/2006 | Fine et al. |
| 7,025,728 B2 | 4/2006 | Ito et al. |
| 7,027,849 B2 | 4/2006 | Al-Ali |
| 7,043,289 B2 | 5/2006 | Fine et al. |
| 7,047,056 B2 | 5/2006 | Hannula et al. |
| 7,062,307 B2 | 6/2006 | Norris et al. |
| 7,113,815 B2 | 9/2006 | O'Neil et al. |
| 7,215,984 B2 | 5/2007 | Diab et al. |
| 7,215,986 B2 | 5/2007 | Diab et al. |
| 7,254,433 B2 | 8/2007 | Diab et al. |
| 7,260,425 B2 | 8/2007 | Chin et al. |
| 7,328,053 B1 | 2/2008 | Diab et al. |
| 7,376,453 B1 | 5/2008 | Diab et al. |
| 7,383,070 B2 | 6/2008 | Diab et al. |
| 7,386,336 B2 | 6/2008 | Fine et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0103423 A1 | 8/2002 | Chin et al. |
| 2002/0111748 A1 | 8/2002 | Kobayashi et al. |
| 2002/0128544 A1 | 9/2002 | Diab et al. |
| 2002/0133068 A1 | 9/2002 | Huiku |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0050541 A1 * | 3/2003 | Wuori ........................ 600/316 |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0097797 A1 | 5/2004 | Porges et al. |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0204636 A1 | 10/2004 | Diab et al. |
| 2004/0230106 A1 | 11/2004 | Schmitt et al. |
| 2004/0267140 A1 | 12/2004 | Ito et al. |
| 2005/0070773 A1 | 3/2005 | Chin et al. |
| 2005/0070775 A1 | 3/2005 | Chin et al. |
| 2005/0080323 A1 | 4/2005 | Kato |
| 2005/0101850 A1 | 5/2005 | Parker |
| 2005/0107676 A1 | 5/2005 | Acosta et al. |
| 2005/0113656 A1 | 5/2005 | Chance |
| 2005/0168722 A1 | 8/2005 | Forstner et al. |
| 2005/0192488 A1 | 9/2005 | Bryenton et al. |
| 2005/0197551 A1 | 9/2005 | Al-Ali et al. |
| 2005/0203357 A1 | 9/2005 | Debreczeny et al. |
| 2005/0209517 A1 | 9/2005 | Diab et al. |
| 2005/0267346 A1 | 12/2005 | Faber et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0030764 A1 | 2/2006 | Porges et al. |
| 2006/0052680 A1 | 3/2006 | Diab |
| 2006/0058683 A1 | 3/2006 | Chance |
| 2006/0195028 A1 | 8/2006 | Hannula et al. |
| 2006/0200014 A1 | 9/2006 | Fine et al. |
| 2006/0217609 A1 | 9/2006 | Diab et al. |
| 2006/0258923 A1 | 11/2006 | Al-Ali et al. |
| 2006/0258924 A1 | 11/2006 | Al-Ali et al. |
| 2006/0258925 A1 | 11/2006 | Al-Ali et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1 | 11/2006 | Hannula et al. |
| 2006/0270920 A1 | 11/2006 | Al-Ali et al. |
| 2006/0276700 A1 | 12/2006 | O'Neil et al. |
| 2006/0281983 A1 | 12/2006 | Al-Ali et al. |
| 2007/0225581 A1 | 9/2007 | Diab et al. |
| 2007/0249918 A1 | 10/2007 | Diab et al. |
| 2007/0260132 A1 | 11/2007 | Sterling |
| 2007/0291832 A1 | 12/2007 | Diab et al. |
| 2007/0299328 A1 | 12/2007 | Chin et al. |
| 2008/0004514 A1 | 1/2008 | Diab et al. |
| 2008/0033266 A1 | 2/2008 | Diab et al. |

| | | |
|---|---|---|
| 2008/0045823 A1 | 2/2008 | Diab et al. |

FOREIGN PATENT DOCUMENTS

| JP | 5-212016 | 8/1993 |
|---|---|---|
| WO | WO 92/20273 | 11/1992 |
| WO | WO 94/03102 | 2/1994 |
| WO | WO 97/49330 | 12/1997 |
| WO | WO 01/45553 A1 | 6/2001 |

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093.

Bongard, Frederic S., et al., "Continuous Dual Oximetry in Surgical critical care—Indications and Limitations," *Annals of Surgery*, vol. 216, No. 1, pp. 60-68 (1992).

Dr. Vijaylakshmi Kamat, "Pulse Oximetry", Indian J. Anaesth 2002; 46(4):261-268.

\* cited by examiner

US 7,848,891 B2

MODULATION RATIO DETERMINATION WITH ACCOMMODATION OF UNCERTAINTY

BACKGROUND OF THE INVENTION

1. Field of the Invention

The present invention relates generally to estimating fluid characteristics (e.g., blood oxygen saturation) in a patient using photospectrometry. In particular, the present invention relates to providing an estimation of blood oxygen saturation of the patient using a regression of light absorption or transmissivity data for two or more signals passed through the blood perfused tissues of the patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Pulse oximetry is a type of photospectrometry and may be defined as a non-invasive technique that facilitates monitoring of a patient's blood flow characteristics. For example, pulse oximetry may be used to measure blood oxygen saturation of hemoglobin in a patient's arterial blood and/or the patient's pulse rate. Specifically, these measurements may be acquired using a non-invasive sensor that passes light (e.g., via a light emitting diode) through a portion of a patient's blood perfused tissue and photo-electrically senses (e.g., via a photo-detector) the absorption and scattering of light through the blood perfused tissue. Data relating to the absorption and scattering of the light may be utilized to calculate the amount of certain constituents in the blood perfused tissue. Such calculations may be based on empirical data relating to light scattering and absorption characteristics associated with specific constituents (e.g., oxyhemoglobin and deoxyhemoglobin) at particular wavelengths.

The accuracy of blood flow characteristic estimations obtained via pulse oximetry depends on a number of factors. For example, variations in light absorption characteristics can affect accuracy depending on where (e.g., finger, foot, or ear) the sensor is positioned on a patient or depending on the physiology of the patient. Additionally, various types of noise and interference can create uncertainties. For example, bright external lights, electrical noise, physiological noise, and such can contribute to inaccurate blood flow characteristic calculations. Accordingly, it is desirable to provide a system and method that accounts for uncertainties or errors in measurement data relating to blood flow characteristic estimation.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention relate generally to estimating fluid characteristics (e.g., blood oxygen saturation) in a patient using photospectrometry. Specifically, embodiments of the present invention are directed to using a regression of light absorption or transmissivity data for two or more signals passed through the blood of a patient to provide an estimation of blood oxygen saturation, wherein the regression accommodates for uncertainty in all or part of the two or more signals. For example, in accordance with present embodiments, an orthogonal-fit or a Principal Component Regression may be utilized in determining a red-to-infrared modulation ratio. An orthogonal-fit may be defined as a regression technique for data with comparable error in each measurement dimension. It should be noted that, as discussed in further detail below, the red-to-infrared modulation ratio may correspond to the oxygen saturation of the arterial blood. Further, it should be noted that embodiments of the present invention are not limited to pulse oximetry. For example, some embodiments may be utilized in other photospectrometry applications, such as the measurement of tissue water fraction and the like.

Figure 1:
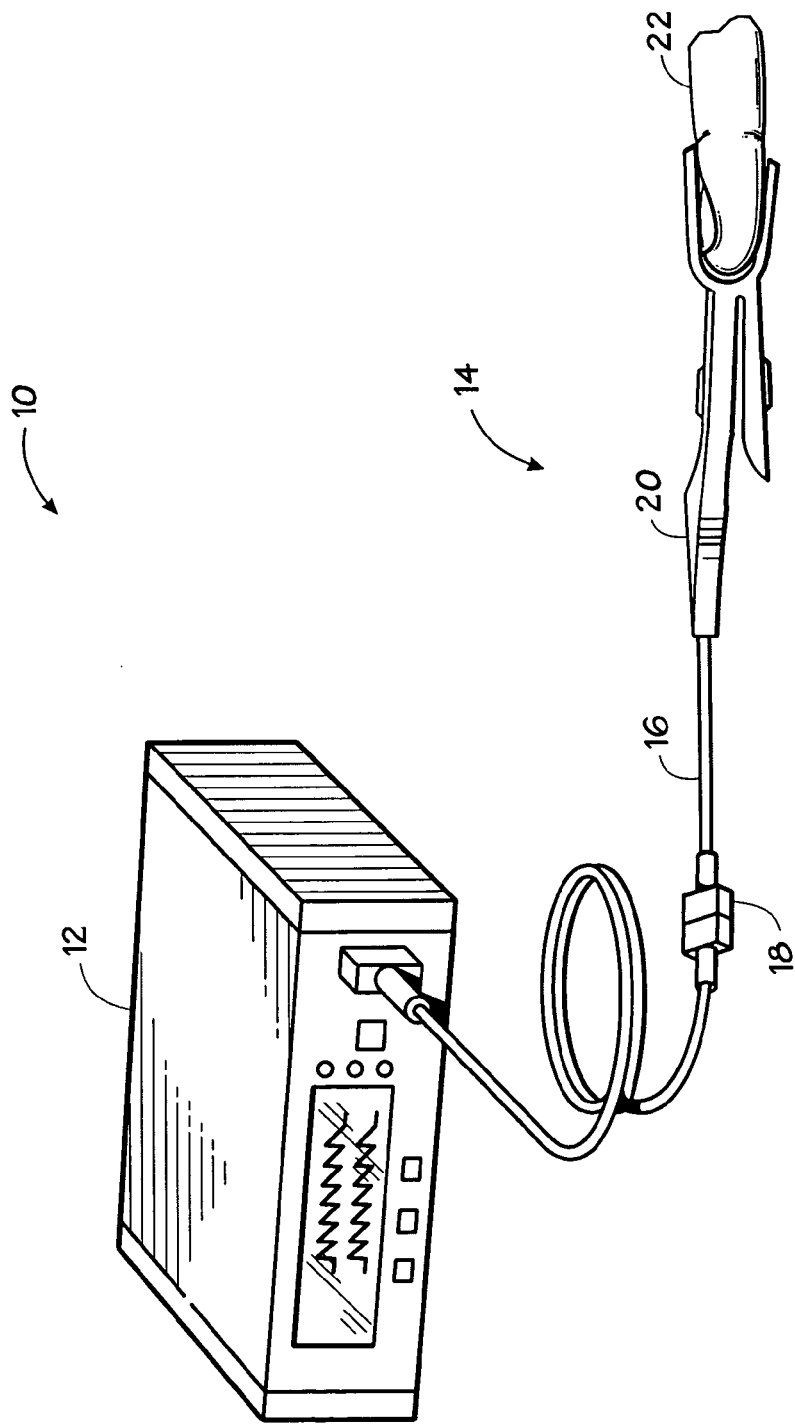
FIG. 1 shows a perspective view of a pulse oximeter system in accordance with an exemplary embodiment of the present invention.

FIG. 1 shows a perspective view of a basic pulse oximeter system 10 in accordance with an exemplary embodiment of the present invention. The system 10 includes a pulse oximeter or monitor 12 that communicatively couples to a sensor 14. The monitor 12 may include various separate components that perform various monitor functions. The sensor 14 may include a sensor cable 16, a connector plug 18, and a body 20 configured to attach to a patient (e.g., patient's finger, ear, forehead, or toe). Pulse oximetry systems such as system 10 may be utilized to observe the oxygenation or oxygen saturation of a patient's arterial blood to estimate the state of oxygen exchange in the patient's body. This may be achieved by emitting signals or waves into the patient's tissue and detecting the waves after dispersion and/or reflection by the tissue. For example, conventional pulse oximeter systems may emit light from two or more light emitting diodes (LEDs) into blood perfused pulsatile tissue (e.g., finger, forehead, toe, or earlobe) and then detect the transmitted light with a light detector (e.g., a photodiode or photo-detector) after the light has passed through the pulsatile tissue.

The amount of transmitted light that passes through the tissue generally varies in accordance with a changing amount of blood constituent in the tissue and the related light absorption. On a beat-by-beat basis, the heart pumps an incremental amount of arterial blood into the tissue, which then drains back through the venous system. The amount of the sensor's emitted light that passes through the blood-perfused tissue varies with the cardiac-induced cycling arterial blood volume. For example, when the cardiac cycle causes more light-absorbing blood to be present in the tissue, less light travels through the tissue to strike the sensor's photo-detector. These pulsatile signals allow pulse oximeters to measure signal attenuation caused by the tissue's arterial blood, because light absorption from other tissues remains generally unchanged in the relevant time scale.

Figure 2:
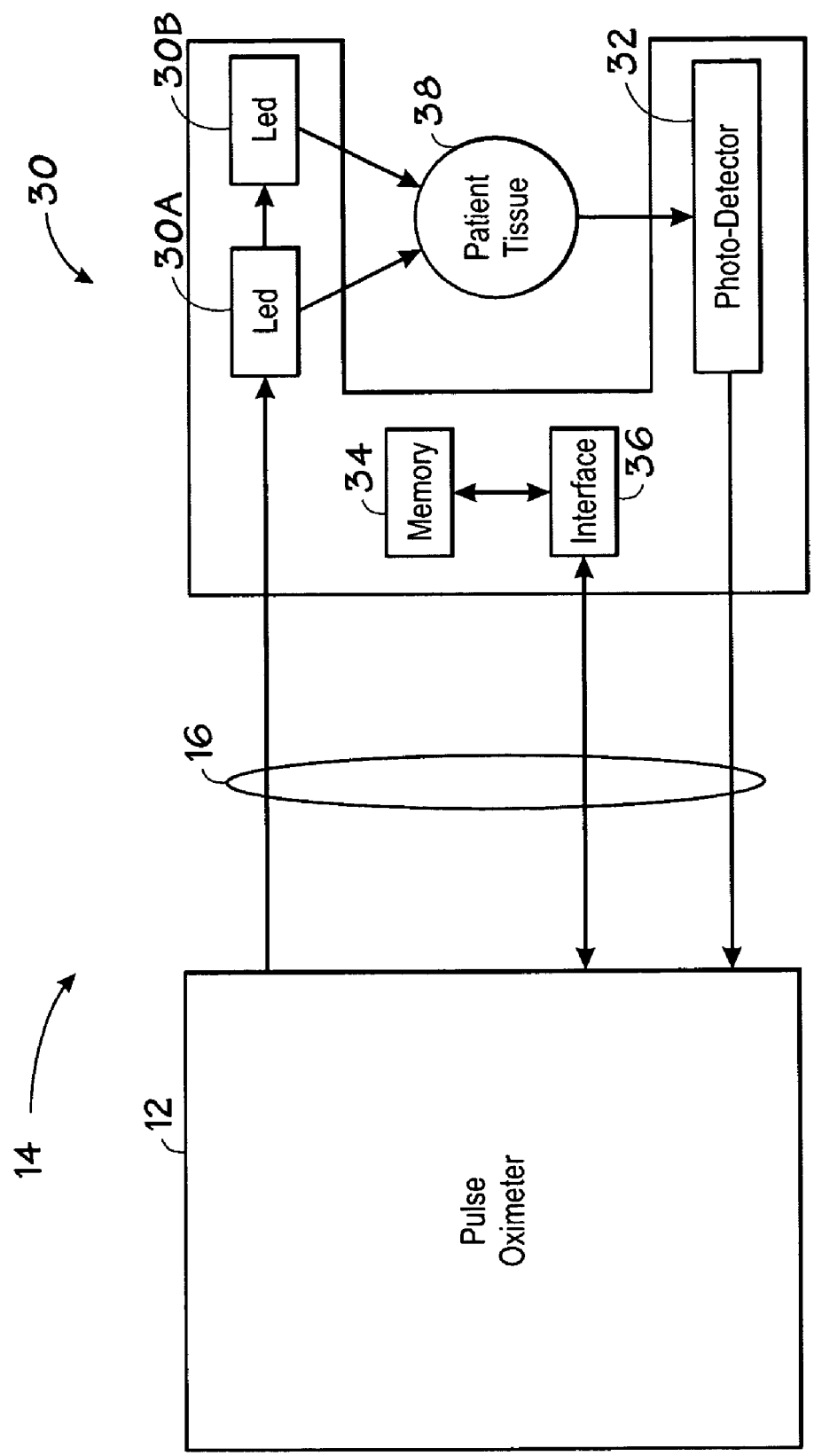
FIG. 2 is a block diagram of a specific embodiment of the sensor that operates in accordance with an exemplary embodiment of the present invention.

FIG. 2 is a block diagram of a specific embodiment of the sensor 14 that operates in accordance with an exemplary embodiment of the present invention. Specifically, as illustrated in FIG. 2, sensor 14 includes two LEDs 30 (i.e., a red LED 30A and an infrared LED 30B) and a photo-detector 32. The illustrated sensor 14 also includes a memory 34 and an interface 36 in accordance with embodiments of the present invention. The LEDs 30 receive drive signals from the monitor 12 that activate the LEDs 30 and cause them to emit signals alternately. The sensor 14 is configured such that light from the activated LEDs 30 can pass into a patient's tissue 38. After being transmitted from or reflected from the tissue 38, the photo-detector 32 receives the dispersed light. The photo-detector 32 then converts the received light into a photocurrent signal, which is eventually provided to the pulse oximeter 12 for processing.

To measure the oxygen saturation of the patient's arterial blood, two different wavelengths of light are typically emitted from the LEDs 30 and are used to calculate the ratio of oxygenated hemoglobin or oxyhemoglobin ($O_2Hb$) to the sum of deoxygenated hemoglobin or deoxyhemoglobin (HHb) and $O_2Hb$. It should be noted that $O_2Hb$ and HHb are dominant hemoglobin components. The light passed through the tissue 38 is typically selected to include two or more wavelengths that are absorbed by the blood in an amount related to the amount of blood constituent present in the blood. Specifically, a first wavelength for one of the LEDs 30 is typically selected at a point in the electromagnetic spectrum where the absorption of $O_2Hb$ differs from the absorption of HHb. A second wavelength for one of the LEDs 30 is typically selected at a different point in the spectrum where the absorption of HHb and $O_2Hb$ differs from that at the first wavelength. For example, LED wavelength selections for measuring normal blood oxygenation levels typically include a red light emitted at approximately 660; nm and an infrared light emitted at approximately 900; nm.

The measurement of blood oxygen via pulse oximetry includes what is essentially an assessment of the relative color of the blood. Different blood constituents often have different light absorption characteristics, which can be utilized to determine constituent quantities (e.g., a percentage of a particular constituent in the blood or tissue). For example, $O_2Hb$ absorbs visible and infrared (IR) light differently than does HHb. Specifically, HHb absorbs more light in the red band than $O_2Hb$, and $O_2Hb$ absorbs more light in the infrared band than HHb. To illustrate, typical arterial blood (highly saturated) appears bright red when viewed in white light because $O_2Hb$ passes the red wavelengths of light while absorbing other colors. On the other hand, venous blood (that is less saturated with oxygen than arterial blood) has a darker brown appearance because HHb molecules have increased light absorption in the red and far-red portion of the spectrum. An assessment of blood's overall color, coming from a linear combination of the red ($O_2Hb$) and the brown (HHb), may be quantified by measuring a relative amount of light transmitted at two locations in the absorption spectrum (e.g., 660; nm and 900; nm). Based on correlations between color and blood constituent concentrations, this measurement of blood color may result in a measure of the blood's oxygen saturation.

Data relating to absorption and scattering of multiple wavelengths of light through a material (e.g., blood perfused tissue 38) may be used with various algorithms to estimate amounts of constituents in the material (e.g., blood constituent in the tissue). For example, the color of a mixture of $O_2Hb$ and HHb in the tissue 38 can be assessed by measuring the relative amounts of red and IR light that pass through the tissue 38, and this assessment may in turn be utilized to determine specific fluid characteristics. Specifically, the blood oxygen saturation of the hemoglobin in arterial blood ($SaO_2$) may be determined by measuring the difference in the absorption spectra of $O_2Hb$ and HHb to determine relative proportions of each form of hemoglobin in the arterial blood. The relative pulse amplitude measured at two locations of the absorption spectrum (i.e., the modulation ratio) relates to the oxygen saturation of the arterial blood, as only the arterial blood content changes periodically with the heart beat. Accordingly, the true arterial $SaO_2$; may be estimated ($SpO_2$) by focusing attention on the cardiac-induced modulating of the red and IR light signals.

The tissue 38 contains arterial, capillary, and venous blood as well as muscle, connective tissue and bone. Therefore, the red and IR signals received from the sensor 14 contain a non-pulsatile component which is influenced by the absorbency of tissue, venous blood, capillary blood, non-pulsatile arterial blood, the intensity of the LEDs 30, and the sensitivity of the photo-detector 32. The pulsatile component of the received signals is an indication of the expansion of the arteriolar bed with arterial blood. The amplitude of the pulsatile component is a very small percentage of the total signal amplitude and depends on the blood volume change per pulse and the underlying $SaO_2$. The received red and infrared signals have an exponential relationship to their respective incident intensities. Therefore, the arguments of the received red and infrared signals have a generally linear relationship, and these received signals can be filtered and mathematically processed using either derivatives or logarithms. The effects of different tissue thicknesses and skin pigmentation can be removed from the received signals by normalizing the processed signal by a term that is proportional to the non-pulsatile portion of the received signal intensity. The ratio of the mathematically processed and normalized red and infrared signals is a number which is theoretically a function of only the concentration of oxyhemoglobin and reduced hemoglobin in the arterial blood.

Various techniques may be utilized to mathematically process the filtered signals received from the sensor 14. For example, one method of processing is based on a derivative technique which finds the relative numerical difference between two successive red measurements. This relative difference results in a red term that is proportional to the product of the red optical absorption and the pulsatile path, provided that the sample rate is rapid enough for the time between measurements to be very small. Taking a similar relative difference between two successive infrared measurements provides an infrared term that is proportional to the product of the infrared optical absorption and the pulsatile path. The pulsatile path components may be identical or assumed to be identical for both red and infrared signals, so that the ratio of the differentiated red and infrared terms cancels out the path length. The effects of different tissue thicknesses and skin pigmentation are essentially removed by normalizing the processed signal by removing the terms that are proportional to the red-and infrared non-pulsatile incident intensities.

Figure 3:
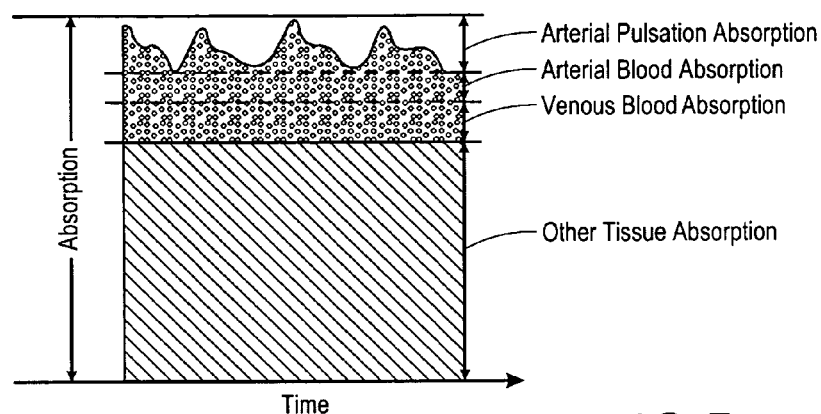
FIG. 3 is a graphical representation of various signal components of a photo-detector signal in accordance with an exemplary embodiment of the present invention.

FIG. 3 is a graphical representation of various components of the signal produced by the photo-detector 32 as a result of a light beam interacting with tissue 38. The light detector output signal consists of a large magnitude non-pulsatile component and a small magnitude pulsatile component. The non-pulsatile component represents light remaining after absorption due to a combination of local venous blood volume, tissue, bone, and constant local arterial blood volume. The small pulsatile component is caused by the light absorption due to local pulsatile arterial blood flow that is to be measured. Since the LEDs 30 are sampled in rapid succession, the data signals produced by the light detector 32 and transmitted to the interface 36 consist of a series of data points which are digitized and stored in memory 34. Further, since the LEDs 30 include red 30A and infrared 30B LEDs, the digitized data points produced consist of a plurality of sets of measurements, with one set corresponding to samples of the red intensity, the other set corresponding to samples of the infrared intensity, and a third set corresponding to ambient light.

Ideally, the ratio of the normalized derivative (or logarithm) of the red intensity to the normalized derivative (or logarithm) of the infrared intensity is a constant. The constant may be indicative of the partial oxygenation of the hemoglobin in the arterial blood flow. This ratio changes as $SpO_2$; changes. However, for a short interval with rapid enough sampling rate, the ratio remains essentially constant. In this system, the key parameter may be referred to as the modulation ratio, "the ratio of ratios" or Ratrat. This parameter may correspond to the ratio of the red arterial optical absorption to the infrared arterial optical absorption. The Ratrat measures the ratio of the normalized derivative (or logarithm) of red intensity to the normalized derivative (or logarithm) of infrared intensity. The significance is that the Ratrat can be understood by examining the optical behavior of light as it passes through tissue. The light is scattered and absorbed by all the tissues, but the light passing through a pulsing artery or arterial bed will pass through a changing path length. The other tissues are essentially unchanging and contribute to the steady non-pulsatile signal, but not to the time-varying pulsatile signals. The absorption of light by arterial blood is assumed to be only a function of the oxygenation state of the hemoglobin. Other assumptions may include that the red and IR light travel along essentially the same optical path, and that all the hardware circuits do not introduce bias into the signal extraction. The measured value of Ratrat is used to compute the $SpO_2$; value.

As would be understood by one of ordinary skill in the art, the mathematical derivation of the Ratrat may be obtained using the Beer-Lambert equation as a base. Exemplary derivations are set forth in U.S. Pat. No. 5,351,685, which is incorporated herein by reference. As indicated above, the Ratrat may be determined using either natural logarithms or derivatives. For example, the Ratrat may be calculated by taking the natural logarithm of the ratio of the value of the peak measurement of a red signal ($Red_p$) divided by the value of the valley measurement of the red signal ($Red_v$). This value, once obtained, may then be divided by the natural logarithm of the ratio of the peak value of the infrared signal ($IR_p$) divided by the value of the valley measurement of the infrared signal ($IR_v$). This is illustrated in the following equation:

$$\text{Ratrat} = (ln(Red_p/Red_v))/(ln(IR_p/IR_v)) \qquad (1)$$

It should be noted that in other embodiments the peak and valley measurements are not necessarily employed to determine the Ratrat. Indeed, the Ratrat may be obtained by using essentially any pair of points along both the infrared and red light waveforms.

In another example, the Ratrat may be calculated by taking the derivative of the Beer-Lambert function. In contrast to the use of peak and valley measurements with the natural logarithm based formula, to calculate the Ratrat according to the derivative based formula, a large number of sampled points along the waveform of the optical signal may be used. In other words, a series of sample points from the red and IR signals may be used for each data point. A derivative may then be calculated for each pair of data points and used to determine the ratio of the derivatives for the red (DRed) and IR (DIR) signals. A plot of DRed versus DIR values (sampled at multiple timesteps) will ideally be linear. While noise components may cause error in some values, the impact of the errors may be reduced by performing a regression and determining a best-fit line. The best-fit line may be used to calculate the Ratrat. An instantaneous value of the Ratrat may be determined by multiplying the ratio of derivatives to the ratio of the measured non-pulsatile intensities for the red ($I_{out\,Red}$) and IR signals ($I_{out\,IR}$). This is illustrated in the following equation:

$$\text{Ratrat} = (I_{out\,IR})(DRed)/(I_{out\,Red})(DIR) \qquad (2)$$

Figure 4:
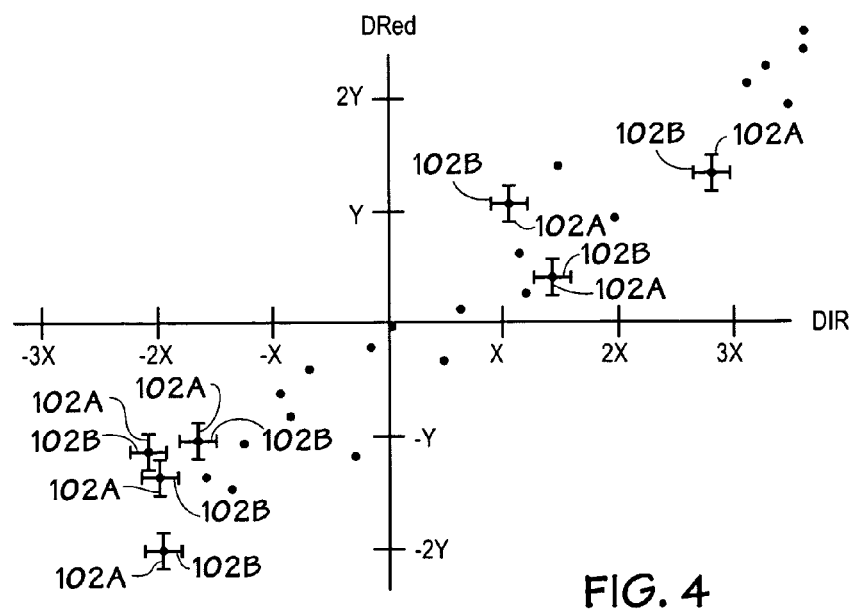
FIG. 4 is a graphical representation of a data set utilized in accordance with an exemplary embodiment of the present invention.

FIG. 4 is a graphical representation of a data set utilized in accordance with present embodiments. Specifically, FIG. 4 illustrates a plot of DRed versus DIR. As noted above, the actual data received by the interface 36 can include fairly significant noise components which are caused by a number of sources. Noise components generally skew the values of both of the magnitudes measured in each set of data points, thus affecting the correct relationship between the red and IR signals and creating uncertainty. Specific error components of the DRed magnitude are designated by reference numeral 102A, and specific error components of the DIR magnitude are designated by reference numeral 102B. While each of the data points has DRed and DIR error components, for illustrative purposes, only select data points are represented with error components 102A and 102B.

Existing pulse oximeter systems generally determine the modulation amplitude ratio or Ratrat by computing a simple linear regression (y=mx+b) of the red versus IR pulsatile signals after taking their respective derivatives or logarithms. In such applications, the slope (m) corresponds to the value of Ratrat. However, this simple linear regression fails to treat the uncertainty 102A and 102B caused by noise (e.g., electrical noise) as coming from both detected signals (i.e., IR and red). Rather, the simple linear regression only accounts for uncertainty in the "dependent" component (e.g., the signal assigned to the y-axis). The "independent variable" (e.g., the signal assigned to the x-axis) is considered as "noise free" in a simple linear regression. Accordingly, it is now recognized that existing techniques generally result in an underestimated value of the slope and Ratrat because they fail to consider the error components 102A and 102B in both variables.

Embodiments of the present technique accommodate uncertainty in each detected signal (e.g., red and IR). This includes embodiments wherein two or more signals are utilized. Specifically, embodiments of the present technique utilize Principal Component Regression or an orthogonal-fit that recognizes uncertainty in both X and Y variables in a plot of detected signals. Present embodiments incorporate the relative values of uncertainties. Accordingly, uncertainty is taken into consideration even if it differs in each signal. For example, if signals are substantially stronger in one channel over another and the gain levels are different, the relative values are still taken into consideration in present embodiments.

Figure 5:
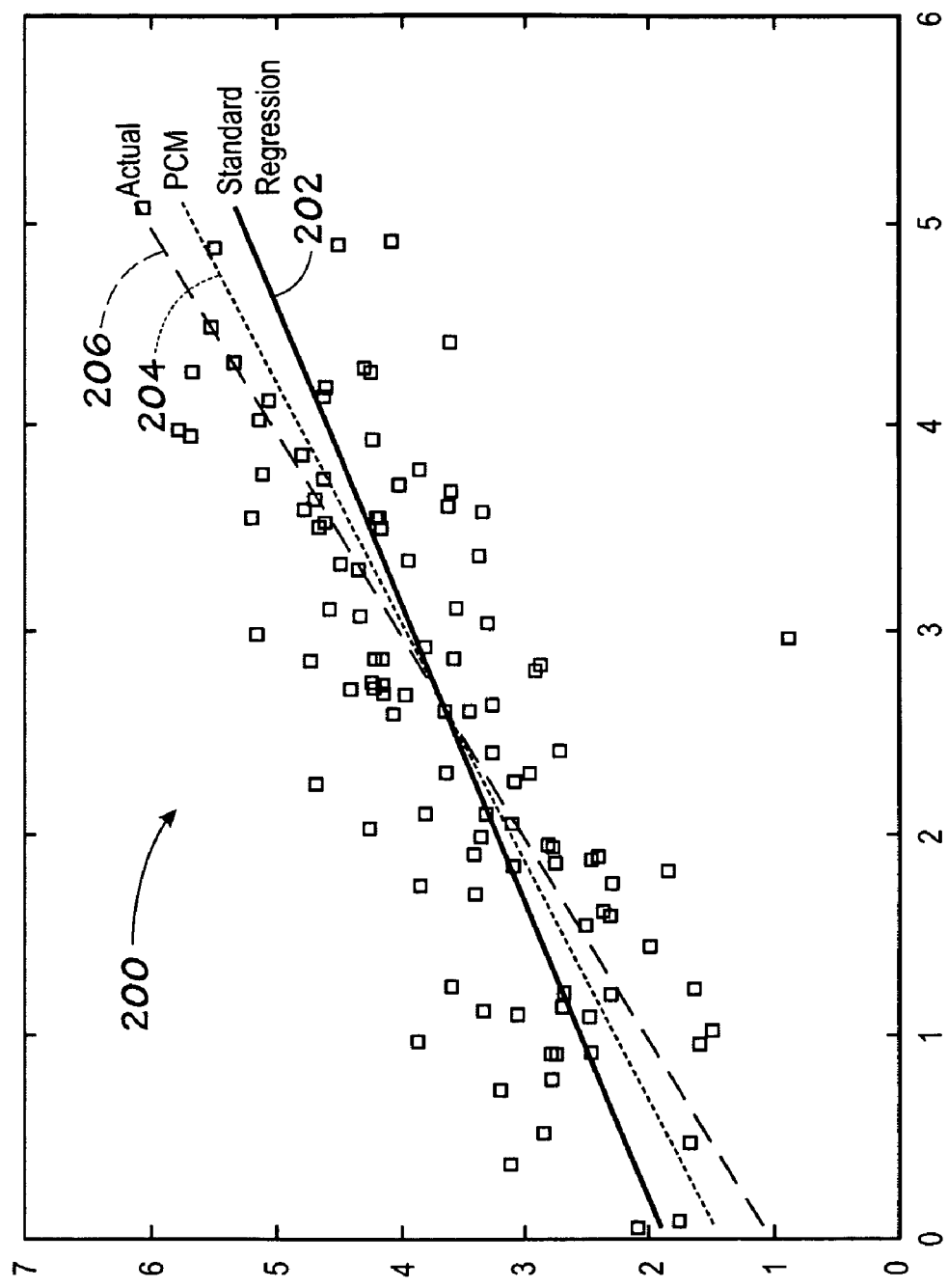
FIG. 5 is a graphical representation of a regression of exemplary photospectrometry signal data in accordance with an exemplary embodiment of the present invention.

FIG. 5 is a graphical representation of a regression of exemplary photospectrometry signal data 200 in accordance with an exemplary embodiment of the present invention. Specifically, FIG. 5 illustrates a comparison of a standard regression 202 (i.e., ordinary least squares) to a Principal Component Regression 204. The two regression types are compared for affinely related data, $\tilde{y}_i = \tilde{x}_i + 1$, with comparable error added in the x- and y-dimensions. The exemplary signal data 200 was generated from an actual true line 206 by essentially introducing noise. As illustrated in FIG. 5, the Principal Component Regression 204 provides a better approximation of the actual true line 206 than does the standard regression 202. Regarding regression, a set of observed data, $\{(x_i, y_i)\}_{i=1}^{k}$, may be assumed to be expressed as true values plus some error:

$$x_i = \tilde{x}_i + \epsilon_i, \ y_i = \tilde{y}_i + n_i, \text{ where}$$

$\epsilon_i$; and $n_i$; are noise, and the true values are affinely related: $\bar{y}_i = m\bar{x}_i + b$ \hfill (3)

The object of regression may be to estimate m and b from the observed data.

Figure 6:
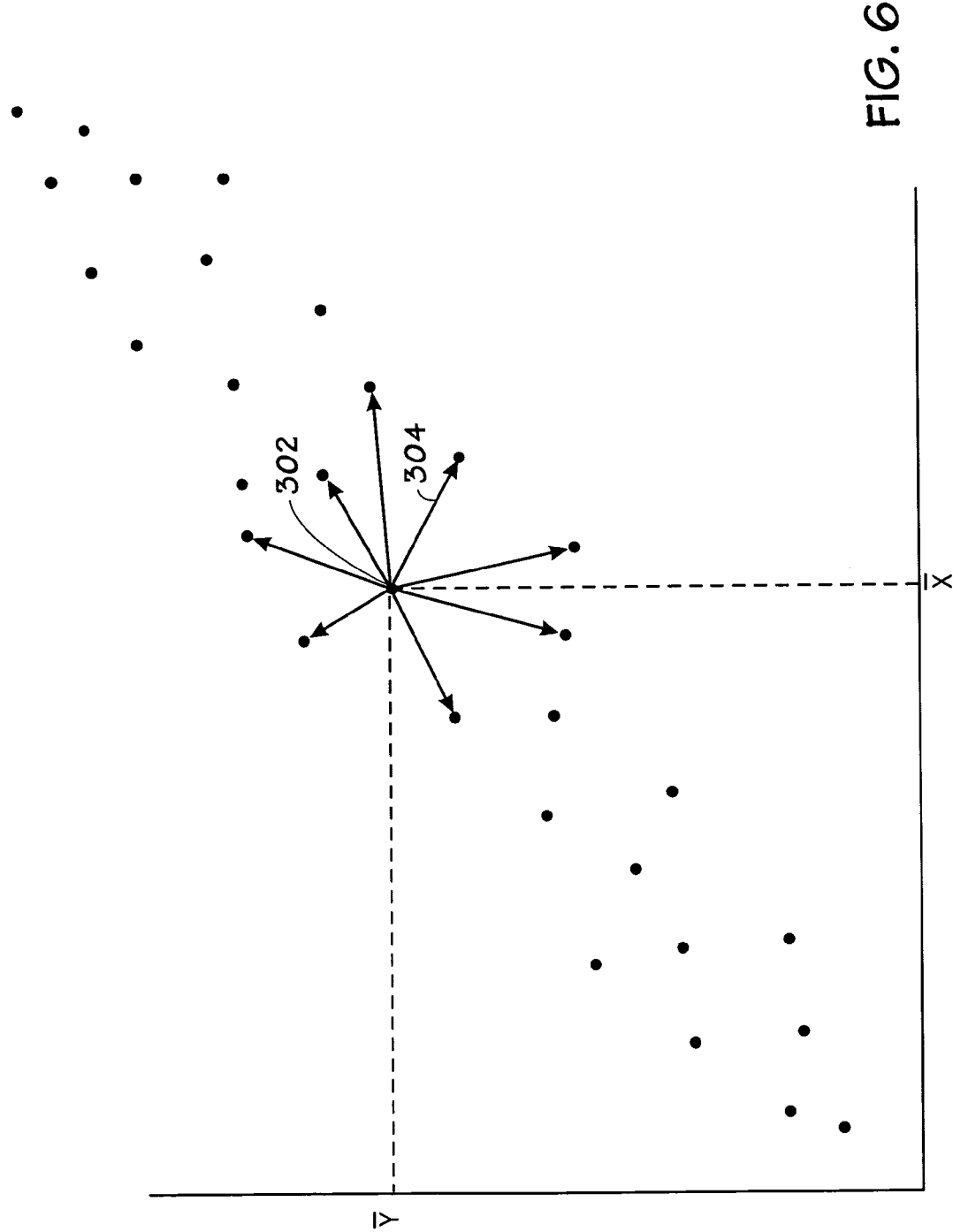
FIG. 6 is a graphical representation of exemplary data points, wherein a mean data point is designated and vectors from the mean data point to each data point are determined to facilitate regression in accordance with an exemplary embodiment of the present invention.

FIG. 6 is a graphical representation of exemplary data points, wherein a mean data point 302 is designated and vectors 304 from the mean data point 302 to each data in the set of data points is determined to facilitate regression. As set forth above, to accommodate uncertainty in each detected signal, a Principal Component Regression may be utilized in accordance with present techniques. Principal Component Regression accounts for uncertainty by taking x- and y-means and accounting for vectors 304 from the mean 302 to the measured data, as illustrated in FIG. 6. This is done for each data point. However, for the sake of clarity, only select data points are shown with corresponding vectors in FIG. 6.

In a Principal Component Regression, $(\bar{x}, \bar{y})$ may represent the x- and y-means. Accordingly, the following equation is appropriate as a vector in 2-space:

$$v_i = \begin{bmatrix} x_i - \bar{x} \\ y_i - \bar{y} \end{bmatrix}. \tag{4}$$

The Principal Component is a vector $\hat{w}$ that has the highest covariance with the vectors $\{v_i\}_{i}^{k}=1$. That is, $\hat{w}$ solves the following maximization problem:

$$\max_{w: w \cdot w = 1} \sum_{i=1}^{k} |v_i * w|^2, \text{ where} \tag{5}$$

* gives the dot product of two vectors.

Once an estimate $\hat{w}$ is known, the data are approximated by the following equation:

$$v_i = g_i \hat{w}, \text{ which is to say that:} \tag{6}$$

$$\begin{aligned} x_i - \bar{x} &= g_i \hat{w}1 \\ y_i - \bar{y} &= g_i \hat{w}2 \end{aligned} \Rightarrow y_i =$$

$$\frac{\hat{w}2}{\hat{w}1} x_i + \left( \bar{y} - \frac{\hat{w}2}{\hat{w}1} \bar{x} \right) = \hat{m} x_i + \hat{b}, \text{ where}$$

$\hat{w}1$ and $\hat{w}2$ are the elements of (the vector)$\hat{w}$.

This establishes a constrained optimization problem, which may be solved by the Lagrange Multiplier Method. The constrained optimization problem essentially reduces to finding vector $\hat{w}$ and scalar $\lambda$ such that:

$$\begin{bmatrix} \sum (x_i - \bar{x})^2 & \sum (x_i - \bar{x})(y_i - \bar{y}) \\ \sum (x_i - \bar{x})(y_i - \bar{y}) & \sum (y_i - \bar{y})^2 \end{bmatrix} \hat{w} = \lambda \hat{w}. \tag{7}$$

That is, $\hat{w}$ is the eigenvector of the above matrix, and $\lambda$ is the associated eigenvalue. Thus there are two possible solutions. Further computation shows that $\hat{w}$ should be the eigenvector associated with the larger eigenvalue $\lambda$, as follows.

$$\text{Let } \alpha = \frac{1}{2} \sum_{i=1}^{k} (x_i - \bar{x})^2, \tag{8}$$

$$\beta = \sum_{i=1}^{k} (x_i - \bar{x})(y_i - \bar{y}), \ \gamma = \frac{1}{2} \sum_{i=1}^{k} (y_i - \bar{y})^2.$$

The eigenvalues and eigenvectors of the matrix $$\begin{bmatrix} 2\alpha & \beta \\ \beta & 2\gamma \end{bmatrix}$$

are:

$$\lambda \pm = (\gamma + \alpha) \pm \sqrt{(\gamma - \alpha)^2 + \beta^2} \tag{9}$$

$$\hat{w} \pm = \left[ 1, \frac{(\gamma - \alpha) \pm \sqrt{(\gamma - \alpha)^2 + \beta^2}}{\beta} \right]^T.$$

This gives approximate affine coefficients:

$$\hat{m} = \frac{(\gamma - \alpha) + \sqrt{(\gamma - \alpha)^2 + \beta^2}}{\beta}, \tag{10}$$

$$\hat{b} = \bar{y} - \hat{m}\bar{x} = \bar{y} - \frac{(\gamma - \alpha) + \sqrt{(\gamma - \alpha)^2 + \beta^2}}{\beta} \bar{x}.$$

The procedures set forth above utilize Principal Component Regression or an orthogonal-fit to recognize comparable uncertainty in at least two detected signals of a photospectrometry device. Further, these procedures incorporate the relative values of the uncertainties into calculations of fluid characteristics being determined via the photospectrometry. Thus, by accommodating uncertainty in each detected signal (e.g., red and IR), present embodiments take uncertainty into consideration even if it differs in each signal. Accordingly, present embodiments improve the reliability and accuracy of blood characteristic estimations, such as blood oxygen content estimations. It should be noted that embodiments of the present invention may be utilized to improve or facilitate measurements related to constituents such as carboxyhemoglobin, methemoglobin, total hemoglobin, bilirubin, glucose, pH, $CO_2$, $H_2O$ and so forth.

Variants of the procedure set forth above may be utilized to accommodate certain limitations (e.g., system memory limitations), facilitate calculation, and so forth. In one embodiment, an infinite impulse response (IIR) variant may be utilized to reduce computational complexities associated with the estimation calculations set forth above. For example, the IIR variant may reduce computational complexity by limiting the amount of historical data (e.g., coordinates of x, y data pairs) retained in memory for calculating blood characteristic estimations and so forth. This may be achieved by essentially devaluing older observations such that more recent observations contribute more to the estimation and incorporating this weighting scheme into a set of reusable equations.

In the IIR variant, it may be assumed that data observations $\{(x_i, y_i)\}_{i=1}^{k}$ are given in increasing chronological order. Further, r may be some number in the closed interval from zero to one (i.e., r may be some number in [0,1]). Accordingly, the Weighted Principal Component regression technique looks for $\hat{w}$ that solves the following equation:

$$\max_{w:w \cdot w=1} \sum_{i=1}^{k} r^{k-i} |u_i \cdot w|^2, \text{ where} \tag{18}$$

$$u_i = \begin{bmatrix} x_i - \breve{x} \\ y_i - \breve{y} \end{bmatrix}, \tag{19}$$

and $\breve{x}$, $\breve{y}$ are the weighted means of the observations, as follows:

$$\breve{x} = \frac{\sum_{i=1}^{k} r^{k-i} x_i}{\sum_{i=1}^{k} r^{k-i}}, \breve{y} = \frac{\sum_{i=1}^{k} r^{k-i} y_i}{\sum_{i=1}^{k} r^{k-i}}, \tag{20}$$

According to the Weighted Principal Component regression technique, as the number of observations (k) increase, the less weighting is given to earlier observations. It should be noted that if r is set to one (i.e., r=1), the solution set forth in Equation 10; applies with $\alpha$, $\beta$, and $\gamma$ values calculated as set forth in Equation 8. In the IIR variant, when r is utilized as a weighting factor (i.e., r may be some number in [0,1]), the solution set forth in Equation 10; carries over but, $\alpha$, $\beta$, and $\gamma$ are defined as follows:

$$\alpha = \frac{1}{2} \sum_{i=1}^{k} r^{k-i}(x_i - \breve{x})^2, \beta = \sum_{i=1}^{k} r^{k-i}(x_i - \breve{x})(y_i - \breve{y}), \tag{21}$$

$$\gamma = \frac{1}{2} \sum_{i=1}^{k} r^{k-i}(y_i - \breve{y})^2,$$

The IIR variant of the algorithm facilitates updating $\hat{m}$ and $\hat{b}$ by reusing some of the information from the previous time step. In other words, given a new observation, $(x_{k+1}, y_{k+1})$, new estimates $\hat{m}_{k+1}$ and $\hat{b}_{k+1}$ may be computed without incurring a computational cost as great as would be required without reusing the information from the previous time step. Previous time step information is essentially incorporated into the algorithm without actually storing all of the historical data values.

The IIR algorithm can be expressed as follows, where r is a weighting factor. As a loop invariant, it may be supposed that:

$$sum = \sum_{i=1}^{k} r^{k-i}, \tag{11}$$

$$sumx = \sum_{i=1}^{k} r^{k-i} x_i, \tag{12}$$

$$sumy = \sum_{i=1}^{k} r^{k-i} y_i, \tag{13}$$

$$sumxx = \sum_{i=1}^{k} r^{k-i} x_i^2, \tag{14}$$

$$sumxy = \sum_{i=1}^{k} r^{k-i} x_i y_i, \tag{15}$$

$$sumyy = \sum_{i=1}^{k} r^{k-i} y_i^2, \tag{16}$$

Equation 11; represents the number of quality observations. Early observations are essentially less quality than more recent observations. Equations 12-16; represent weighting values for various data combinations. The weighting values are utilized to calculate $\alpha$, $\beta$, and $\gamma$, as set forth below. These equations may be updated at every time step. Each update of the loop may be given as:

$$sum \leftarrow r\ sum + 1, \tag{17}$$

$$sumx \leftarrow r\ sumx + x_{k+1},$$

$$sumy \leftarrow r\ sumy + y_{k+1},$$

$$sumxx \leftarrow r\ sumxx + x_{k+1}^2,$$

$$sumxy \leftarrow r\ sumxy + x_{k+1} y_{k+1},$$

$$sumyy \leftarrow r\ sumyy + y_{k+1}^2,$$

$$\alpha \leftarrow \frac{1}{2}(sumxx - sumx^2/sum),$$

$$\beta \leftarrow sumxy - (sumx)(sumy)/sum,$$

-continued $$\gamma \leftarrow \frac{1}{2}(sumyy - sumy^2/sum),$$

$$ga \leftarrow \gamma - \alpha,$$

$$\hat{m} \leftarrow (ga + \sqrt{ga^2 + \beta^2})/\beta,$$

$$\hat{b} \leftarrow (sumy - (\hat{m})(sumx))/sum.$$

Figure 7:
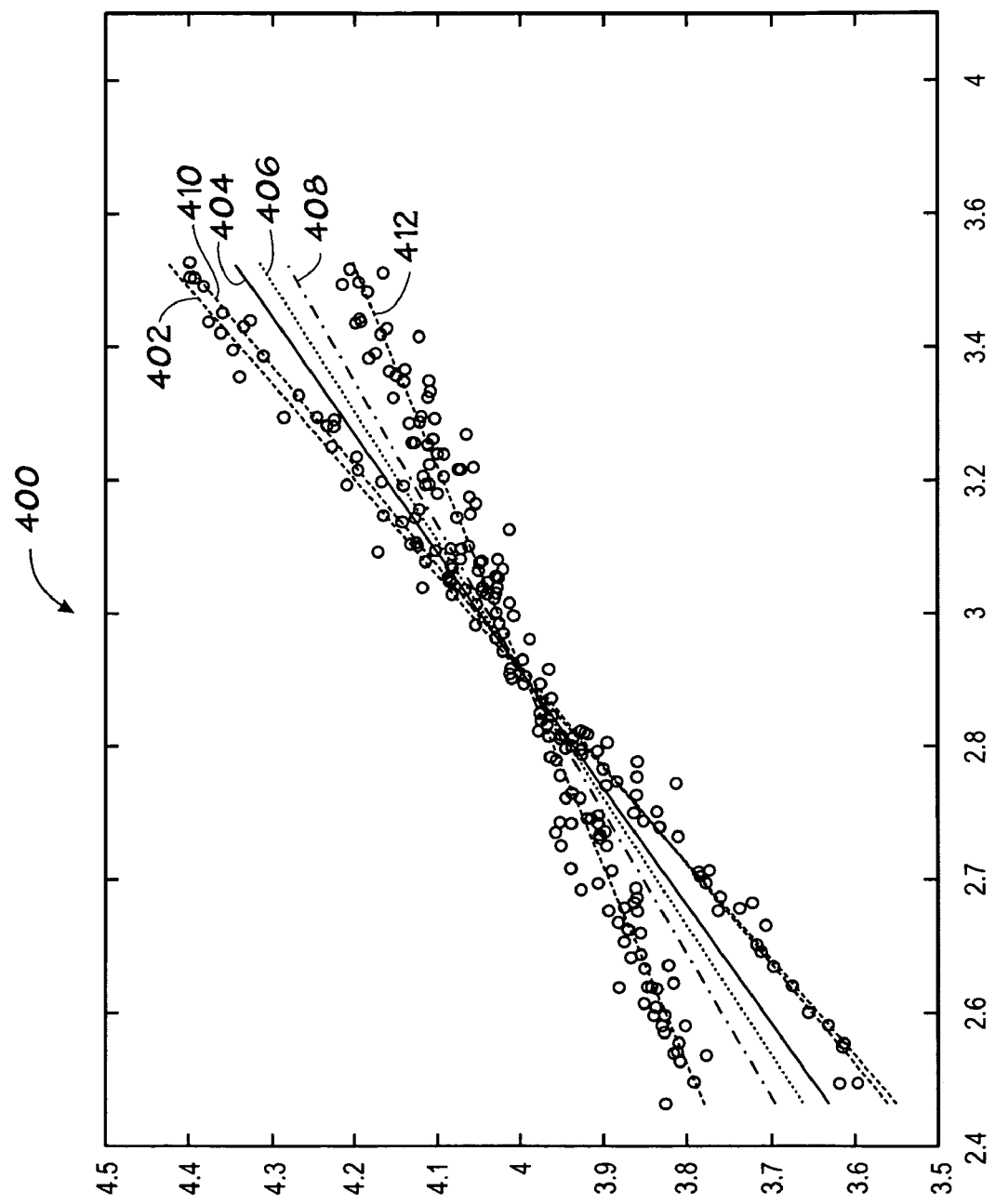
FIG. 7 is a plot providing a graphical representation of IIR variant behavior for different values of r in accordance with an exemplary embodiment of the present invention.

FIG. 7 is a plot 400 providing a graphical representation of the behavior of an IIR variant for different values of r in accordance with an exemplary embodiment of the present invention. By varying the factor r, different estimates of the slope may be obtained. Smaller values of r will downweight the older observations so much the result will essentially be $(m_2, b_2)$+random error. Larger values of r (e.g., near 1) will give a mix of $m_1$; and $m_2$. The data in FIG. 7 includes 150; points sampled from $y=m_1x=b_1$, followed by 80; points sampled from $y=m_2x+b_2$, with $m_1=\frac{1}{3}$, and $m_2=\frac{2}{3}$. The two data modes were parameterized to have the same x and y means. Further, observational noise at equivalent levels was added to the x and y. The data were then passed to the IIR variant of the algorithm, with r values of 0.78, 0.99, 0.995, and 1.0. Fit lines 402, 404, 406, and 408 are plotted along with the noised data and two true lines 410 and 412. Line 402 is the line for which r is approximately 0.78; line 404 in the line for which r is approximately 0.99; line 406 is the line for which r is approximately 0.995; and line 408 is the line for which r is approximately 1.0. As expected, small values of r essentially fit to the most recent data (e.g., true line 410), while larger values of r represent a greater weighting of older values (e.g., samples from true line 412). Thus, the fit lines are a compromise between the two true lines 410 and 412 for larger values of r.

The orthogonal fitting technique may be appropriate when the noise levels in the x and y are assumed to be nearly equal. However, when there are significant errors in the x and y, but at different levels, a preprocessing step may be necessary. In this preprocessing step, the x and y values may be rescaled (e.g., multiplied) so that they have nearly equal noise levels. Thus for example, if the model of the data is equation (3), and it is known that the standard deviation of $e_i$; is about k times the standard deviation of $n_i$, then all observed $y_i$; values may be multiplied by k to make the noise levels equal. Once this is done, the regressed slope and intercept may be transformed back. Particularly, the slope may be multiplied by (1/k) to recover the fit to the original data. This may result in a different estimate of the slope than if the scaling had not been performed.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of detecting a blood characteristic in a patient, comprising:
    identifying a plurality of first modulating signal values with a processor based on detecting a first modulating signal at a first wavelength with a detector over a time period;
    identifying a plurality of second modulating signal values with the processor based on detecting a second modulating signal at a second wavelength with the detector over the time period; and
    determining a relative amplitude of the first and second modulating signal values with the processor comprising:
        weighting the first and second modulating signal values with non-zero weighting factors such that more weighting is given to values identified later in the time period and less weighting is given to values identified earlier in the time period; and
        regressing the first and second modulating signal values relative to one another, wherein a first uncertainty value in the first modulating signal and a second uncertainty value in the second modulating signal are accommodated and the non-zero weighting factors are incorporated.

2. The method of claim 1, comprising determining a best-fit relationship based on the regressing of the first and second modulating signal values.

3. The method of claim 2, comprising calculating a blood oxygen level, a carboxyhemoglobin level, a methemoglobin level, a total hemoglobin, a bilirubin level, a glucose level, a pH, or $CO_2$ level based on the best-fit relationship.

4. The method of claim 1, wherein the first and second modulating signals comprise photoplethysmographic signals.

5. The method of claim 1, wherein the first uncertainty value is non-zero and the second uncertainty value is non-zero.

6. The method of claim 1, wherein the first and second uncertainty values are not equal.

7. The method of claim 1, wherein regressing the first and second modulating signal values includes performing an orthogonal fit.

8. The method of claim 1, wherein regressing the first and second modulating signals includes performing a Weighted Principal Component regression.

9. The method of claim 1, wherein regressing the first and second modulating signal values includes determining mean values of data points from the first and second modulating signals.

10. The method of claim 9, comprising defining a mean data point from the mean values of the data points and defining vectors from the mean data point to each of the data points.

11. The method of claim 1, comprising calculating a blood oxygen level based on the relative amplitude.

12. A system for detecting a blood characteristic in a patient, comprising:
    a detector configured to detect a first modulating signal at a first wavelength and a second modulating signal at a second wavelength after dispersion of the first modulating signal and the second modulating signal by tissue; and
    a monitor configured to:
        determine a plurality of first modulating signal values over a time period based on detection of the first modulating signal;
        determine a plurality of second modulating signal values over the time period based on detection of the second modulating signal;
        assign non-zero weighting values to the first and second modulating signal values such that more weighting is given to values identified later in the time period and less weighting is given to values identified earlier in the time period; and regress the first and second modulating signal values relative to one another while incorporating the non-zero weighting values and accommodating a first uncertainty value in the first modulating signal and a second uncertainty value in the second modulating signal to determine a relative amplitude of the first and second modulating signals.

13. The system of claim 12, wherein the monitor is configured to determine a best-fit relationship based on the regressing of the first and second modulating signal values.

14. The system of claim 12, wherein the monitor is configured to calculate a blood oxygen level, a carboxyhemoglobin level, a methemoglobin level, a total hemoglobin, a bilirubin level, a glucose level, a pH, or $CO_2$ level based on the best-fit relationship.

15. The system of claim 12, wherein the first uncertainty value is non-zero and the second uncertainty value is non-zero.

16. The system of claim 12, wherein the first and second uncertainty values are not equal.

17. The system of claim 12, wherein the monitor is configured to regress the first and second modulating signal values by performing an orthogonal fit.

18. The system of claim 12, wherein the monitor is configured to regress the first and second modulating signals by performing a Weighted Principal Component regression.

19. The system of claim 12, wherein the monitor is configured to regress the first and second modulating signal values by determining mean values of data points from the first and second modulating signals.

20. The system of claim 19, wherein the monitor is configured to define a mean data point from the mean values of the data points and define vectors from the mean data point to each of the data points.

21. The system of claim 12, wherein the monitor is configured to calculate a blood oxygen level based on the relative amplitude.

22. The system of claim 12, comprising an emitter configured to emit the first modulating signal at the first wavelength and the second modulating signal at the second wavelength into the tissue.

23. A method of detecting a blood characteristic in a patient over a time period, comprising:
    emitting a first modulating signal at a first wavelength into tissue from a first emitter;
    emitting a second modulating signal at a second wavelength into the tissue from a second emitter;
    detecting the first modulating signal after dispersion by the tissue with a detector;
    detecting the second modulating signal after dispersion by the tissue with the detector;
    assigning non-zero weighting factors to measured values for the first and second modulating signals with a processor such that more weighting is given to values identified later in the time period and less weighting is given to values identified earlier in the time period;
    regressing the first and second modulating signals relative to one another with the processor, wherein a first uncertainty value in the first modulating signal and a second uncertainty value in the second modulating signal are accommodated; and
    determining a relative amplitude of the first and second modulating signals based on the regressing of the first and second modulating signals relative to one another with the processor, wherein the non-zero weighting factors are incorporated.

24. The method of claim 23, comprising determining a best-fit relationship based on the regressing of the first and second modulating signals.

25. The method of claim 23, wherein the first uncertainty value is non-zero and the second uncertainty value is non-zero.

26. The method of claim 23, wherein the first and second uncertainty values are not equal.

27. The method of claim 23, wherein regressing the first and second modulating signals includes performing an orthogonal fit.

28. The method of claim 23, wherein regressing the first and second modulating signals includes performing a Weighted Principal Component regression.

29. The method of claim 23, wherein regressing the first and second modulating signals includes determining mean values of data points from the first and second modulating signals.

30. The method of claim 1, comprising performing a preprocessing step wherein a determination is made as to whether there is a difference in a level of the first uncertainty value and a level of the second uncertainty value, and rescaling the first and/or second uncertainty values such that the levels of the first and second uncertainty values are nearly equal when the difference is detected.

31. The system of claim 12, wherein the monitor is configured to perform a preprocessing step wherein a determination is made as to whether there is a difference in a level of the first uncertainty value and a level of the second uncertainty value, and rescaling the first and/or second uncertainty values such that the levels of the first and second uncertainty values are nearly equal when the difference is detected.

32. The method of claim 23, comprising performing a preprocessing step wherein a determination is made as to whether there is a difference in a level of the first uncertainty value and a level of the second uncertainty value, and rescaling the first and/or second uncertainty values such that the levels of the first and second uncertainty values are nearly equal when the difference is detected.

* * * * *